(12) United States Patent
Stack et al.

(10) Patent No.: US 6,833,002 B2
(45) Date of Patent: Dec. 21, 2004

(54) STENT DELIVERY CATHETER ASSEMBLY AND METHOD OF USE

(75) Inventors: Richard S. Stack, Chapel Hill, NC (US); Udayan Patel, San Jose, CA (US); William J. Boyle, Temecula, CA (US); Kent C. B. Stalker, San Marcos, CA (US); Paul F. Muller, San Carlos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 283 days.

(21) Appl. No.: 09/885,468

(22) Filed: Jun. 19, 2001

(65) Prior Publication Data

US 2001/0037126 A1 Nov. 1, 2001

Related U.S. Application Data

(62) Division of application No. 09/439,692, filed on Nov. 15, 1999, now Pat. No. 6,264,671.

(51) Int. Cl.[7] .................................................. A61F 2/06
(52) U.S. Cl. ..................................... 623/1.11; 606/194
(58) Field of Search .............................. 606/194, 159, 606/161, 192, 200; 623/1.11; 604/103.09

(56) References Cited

U.S. PATENT DOCUMENTS

| | | |
|---|---|---|
| 3,435,826 A | 4/1969 | Fogarty |
| 3,467,101 A | 9/1969 | Fogarty et al. |
| 3,467,102 A | 9/1969 | Fogarty et al. |
| 3,540,431 A | 11/1970 | Mobin-Uddin |
| 3,635,223 A | 1/1972 | Klieman |
| 3,896,815 A | 7/1975 | Fettel et al. |
| 3,923,065 A | 12/1975 | Nozick et al. |
| 3,978,863 A | 9/1976 | Fettel et al. |
| 3,996,938 A | 12/1976 | Clark, III |
| 4,030,503 A | 6/1977 | Clark, III |
| 4,494,531 A | 1/1985 | Gianturco |
| 4,561,439 A | 12/1985 | Bishop et al. |
| 4,594,996 A | 6/1986 | Ibrahim et al. |
| 4,597,389 A | 7/1986 | Ibrahim et al. |
| 4,646,736 A | 3/1987 | Auth |
| 4,762,130 A | 8/1988 | Fogarty et al. |
| 4,790,812 A | 12/1988 | Hawkins, Jr. et al. |
| 4,873,978 A | 10/1989 | Ginsburg |
| 4,969,891 A | 11/1990 | Gewertz |
| 5,011,488 A | 4/1991 | Ginsburg |
| 5,053,008 A | 10/1991 | Bajaj |
| 5,092,839 A * | 3/1992 | Kipperman ................... 604/53 |
| 5,108,419 A | 4/1992 | Reger et al. |
| 5,112,347 A | 5/1992 | Taheri |

(List continued on next page.)

FOREIGN PATENT DOCUMENTS

WO    WO 97/17100    5/1997

Primary Examiner—Michael J. Milano
Assistant Examiner—D. Jacob Davis
(74) Attorney, Agent, or Firm—Fulwider Patton Lee & Utecht LLP

(57) ABSTRACT

A deformable sheath is attached to a catheter and introduced intravascularly to be expanded against an arterial wall and entrap plaque therebetween. A stent is subsequently deployed within the expanded sheath and the sheath is then withdrawn from within the vasculature to leave the stent expanded against the arterial wall with the plaque entrapped therebetween.

26 Claims, 5 Drawing Sheets

U.S. PATENT DOCUMENTS

| | | |
|---|---|---|
| 5,152,777 A | 10/1992 | Goldberg et al. |
| 5,158,548 A | 10/1992 | Lau et al. |
| 5,160,342 A | 11/1992 | Reger et al. |
| 5,192,286 A | 3/1993 | Phan et al. |
| 5,192,290 A | 3/1993 | Hilal |
| 5,242,399 A | 9/1993 | Lau et al. |
| 5,300,086 A | 4/1994 | Gory et al. |
| 5,320,604 A * | 6/1994 | Walker et al. |
| 5,329,942 A | 7/1994 | Gunther et al. |
| 5,344,426 A | 9/1994 | Lau et al. |
| 5,370,609 A | 12/1994 | Drasler et al. |
| 5,370,657 A | 12/1994 | Irie |
| 5,376,100 A | 12/1994 | Lefebvre |
| 5,383,887 A | 1/1995 | Nadal |
| 5,411,509 A | 5/1995 | Hilal |
| 5,415,630 A | 5/1995 | Gory et al. |
| 5,484,424 A | 1/1996 | Cottenceau et al. |
| 5,507,768 A | 4/1996 | Lau et al. |
| 5,540,707 A | 7/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,643,278 A * | 7/1997 | Wijay ........................ 623/1.11 |
| 5,662,671 A | 9/1997 | Barbut et al. |
| 5,681,347 A | 10/1997 | Cathcart et al. |
| 5,695,507 A | 12/1997 | Auth et al. |
| 5,695,518 A | 12/1997 | Laerum |
| 5,695,519 A | 12/1997 | Summers et al. |
| 5,702,413 A | 12/1997 | Lafontaine |
| 5,769,816 A | 6/1998 | Barbut et al. |
| 5,961,536 A * | 10/1999 | Mickley et al. .............. 606/194 |
| 6,019,777 A * | 2/2000 | Mackenzie ................... 606/198 |

\* cited by examiner

STENT DELIVERY CATHETER ASSEMBLY AND METHOD OF USE

This application is a divisional of application Ser. No. 09/439,692, filed Nov. 15, 1999, now U.S. Pat. No. 6,264, 671.

BACKGROUND OF THE INVENTION

1. Field of the Invention

The present invention relates to angioplasty procedures, and more particularly to a device and method to prevent arterial plaque from being dislodged from the arterial wall in procedures such as, for example, percutaneous transluminal coronary angioplasty (PTCA) or percutaneous transluminal angioplasty (PTA), especially carotid PTA, and migrating into the patient's vasculature.

In typical carotid PTA procedures, a guiding catheter or sheath is percutaneously introduced into the cardiovascular system of a patient through the femoral arteries and advanced through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

A danger always present during any intravascular procedure is the potential for particles of the atherosclerotic plaque, which can be extremely friable, breaking away from the arterial wall. These emboli can subsequently migrate through the patient's vasculature to sensitive organs such as the brain, where they may induce trauma.

2. Description of the Prior Art

The majority of devices that have been proposed to prevent the problem of emboli generated during an angioplasty procedure fall into either of two broad categories: devices that simply intercept emboli flowing within the patient's blood stream, and devices that intercept as well as remove such emboli from within the patient's body. A device typical of the first category is described by Goldberg in U.S. Pat. No. 5,152,777 and consists of a filter comprised of a plurality of resilient, stainless steel wire arms joined at one end so as to form a conical surface, and having rounded tips at their other ends to prevent damage to the vessel walls. Alternatively, the filter may be attached to a catheter through which lysing agents can be introduced to dissolve any trapped emboli. Most devices of this type are intended for permanent deployment within the patient's body, and thus pose the risk of trapping sufficient emboli to adversely affect the flow of blood within the vessel in which they are deployed. Furthermore, any foreign object in the body tends to provoke a response from the immune system and over time can lead to endothelial cell formation.

Devices that remove emboli from the blood stream are similar to the filter devices described above and are typically connected to a deployment device such as a catheter that permits their withdrawal from the vasculature. U.S. Pat. No. 4,969,891 to Gewertz, for example, discloses a removable vascular filter permanently attached to a wire sufficiently long to extend out of the patient when the filter is deployed within. The filter is comprised of a bundle of wires secured together and having end portions that flare outwards to form the actual filter element. The filter is introduced through a catheter and the filter wires expand on their own once released from the catheter to obstruct the vessel and strain the blood flowing therethrough. This device, and others like it, are not adapted for permanent deployment within the body and can only be used for limited periods of time, limiting their efficacy.

In light of the above, it becomes apparent that there remains a need for a device or method that will prevent friable plaque from breaking away from arterial walls during intravascular procedures and forming emboli in the bloodstream, that is easy and safe to deploy, and that may be easily removed or alternatively employed over extended periods of time with minimal adverse impact or immunological response.

SUMMARY OF THE INVENTION

The present invention addresses the above mentioned need by providing a sheath at the distal tip of a catheter to be expanded against an arterial wall and trap plaque therebetween. A stent or other intravascular graft subsequently can be partially deployed distally of the plaque, the sheath then can be removed, and the stent fully expanded to trap the arterial plaque and any emboli between the stent and the arterial wall.

Thus, in one aspect, it is an object of the present invention to provide a device for trapping plaque against a vascular wall comprising an expandable sheath mounted to the distal end of an elongated tube such as a catheter, the sheath to be expanded by a balloon against a mass of atherosclerotic plaque site lining the intima of a body vessel. In another aspect of the present invention, the expandable sheath is reinforced by an expandable element embedded within it.

In yet another aspect of the present invention, an assembly is provided for trapping plaque against a vascular wall comprising an expandable sheath mounted to the distal end of an elongated tube such as a perfusion catheter, a delivery catheter axially slidably disposed within the perfusion catheter, a self-expanding intravascular device such as a stent disposed within the distal tip of the delivery catheter, and a pusher rod axially slidably disposed within the delivery catheter.

It is a further object of the present invention to provide a method for trapping plaque against a vascular wall comprising the steps of expanding a sheath mounted to the distal end of an elongated tube such as a perfusion catheter against the plaque, inserting within the perfusion catheter a delivery catheter with a self-expanding intravascular device such as a stent or intravascular graft disposed within its distal end and a pusher rod disposed adjacent the intravascular device, positioning the delivery catheter distal tip within the expanded sheath, partially withdrawing the delivery catheter to allow the distal portion of the intravascular device to expand against the vessel wall at a location distal of the plaque, withdrawing the expanded sheath, and withdrawing the delivery catheter to expose the rest of the intravascular device and thus allow it to fully expand and trap the plaque against the vessel wall.

DETAILED DESCRIPTION OF THE PREFERRED EMBODIMENTS

Figure 1A:
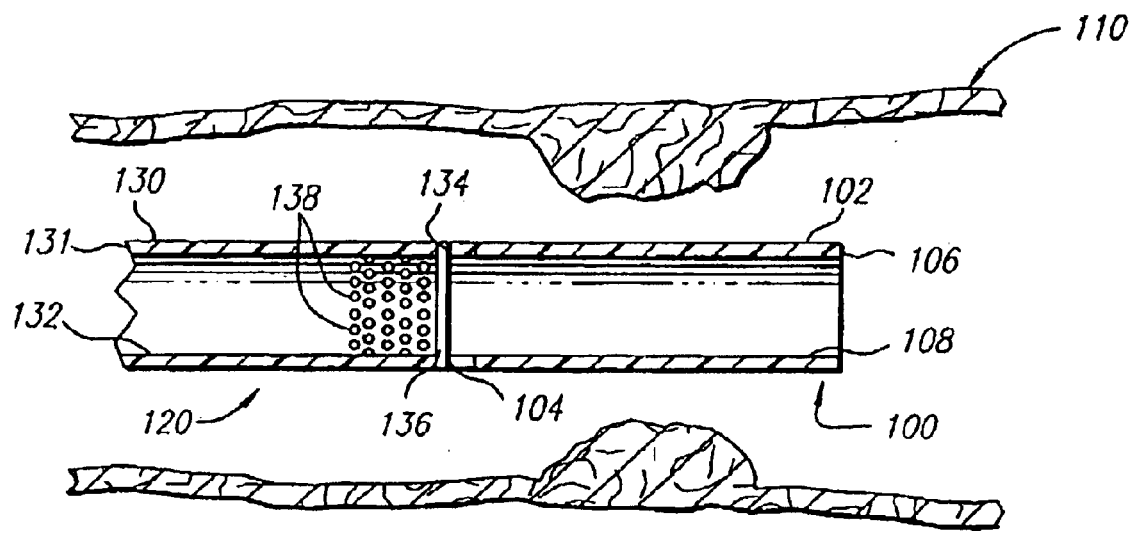
FIG. 1a depicts a cross-sectional side view of an expandable sheath device according to the present invention inserted into a body vessel at an atherosclerotic plaque site.

With reference to FIG. 1a, wherein a preferred embodiment of the catheter assembly and expandable sheath device of the present invention is depicted in its operating environment, expandable sheath 100 is comprised of a tubular wall 102 with a proximal end 104 and a distal end 106, and defining an inner lumen 108 extending therebetween. Sheath 100 as depicted in FIG. 1a is in its unexpanded configuration.

With continued reference to FIG. 1a, sheath 100 preferably is connected to a delivery/deployment device 120 that can introduce the sheath into a patient's body lumen 110 and advance it to the desired deployment site. Insertion device 120 is preferably an elongated tubular member such as catheter 130 depicted in FIG. 1a, with catheter wall 131 defining inner lumen 132 which extends from distal end 134 to a proximal end [not shown] that remains outside of the patient's body. Radiopaque marker 136 is disposed at distal end 134 to enable a physician to precisely position the catheter and sheath with the aid of fluoroscopy.

In a preferred embodiment, catheter 130 is a perfusion catheter provided with perfusion holes 138 formed near distal end 134. Perfusion holes 138 extend from the outside of catheter 130 through catheter wall 131 to inner lumen 132 to allow blood or any other fluid flowing through body lumen 110 to pass between the outside of the catheter and the inner lumen. This feature allows the sheath of the present invention and its associated delivery device to be deployed within a patient's vasculature for extended periods of time without blocking the patient's blood flow. In a preferred embodiment, blood flow through the perfusion holes will be somewhat less than normal blood flow which will lessen the chance of dislodging particles, and if particles are dislodged, the emboli will move more slowly in the reduced blood flow and will be easier to trap in sheath 100.

Sheath 100 is formed from a permanently deformable material, preferably a polymeric material such as a low or medium molecular weight polyolefin, examples of which include PE, EVAc, EVA, and Ionomers. Any other plastically deformable material or blend of materials, including cross-linked materials and composites, may be suitable. The material, once formed into sheath 100, should preferably display a plastic yield strength of between 50 psi and 300 psi, and a tensile break strength of over 2,000 psi. The catheter is of conventional construction with an inner diameter of preferably no less than 8 French in size. Sheath 100 may be attached to distal end 134 of catheter 130 by any known means, such as adhesives or thermoplastics, or may be formed integrally as one piece with the catheter wall 131 through any known extrusion, drawing, rolling, or similar process.

Figure 1B:
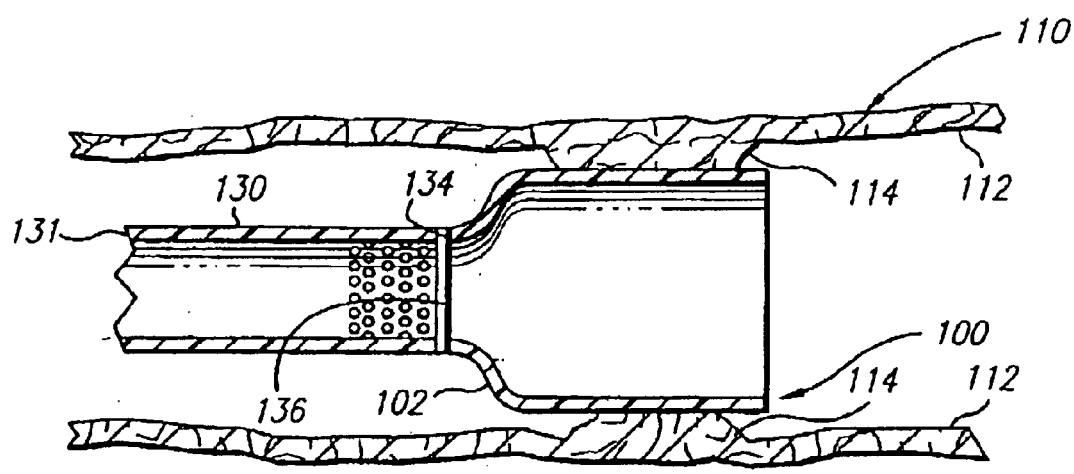
FIG. 1b depicts a cross-sectional side view of the device shown in FIG. 1a with the sheath in an expanded configuration.

With reference now to FIG. 1b, when formed from a material such as described above, sheath 100 is plastically deformable by a typical angioplasty balloon. When expanded by such a balloon, sheath 100 assumes the expanded configuration depicted in FIG. 1b, wherein the sheath is deployed against vascular wall 112 and any arterial plaque 114 deposited thereon, thus compressing and trapping the plaque against the vascular wall.

Figure 2A:
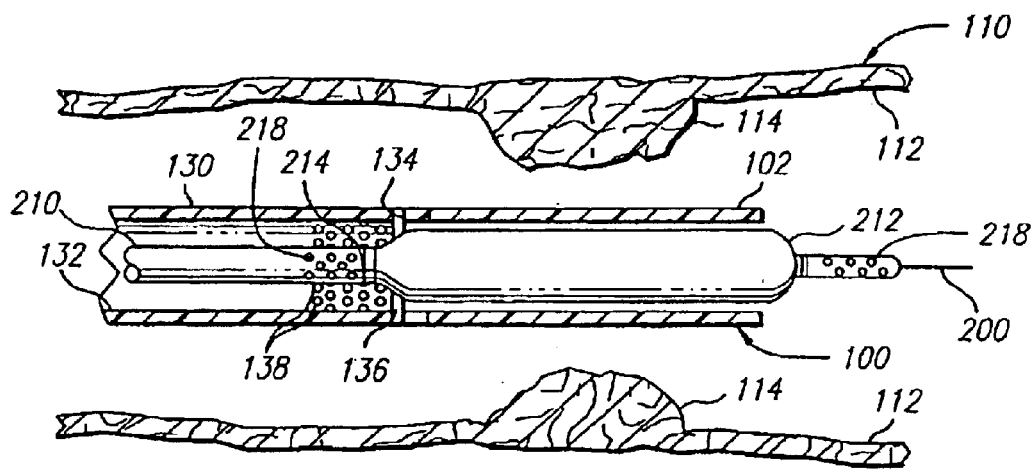
FIG. 2a depicts a side view, partially in cross-section, of the device shown in FIG. 1 a with a balloon catheter inserted therethrough.

In keeping with the invention, as shown in FIG. 2a, in a preferred method of use of the device of the present invention, guidewire 200 is first inserted percutaneously in a conventional manner and advanced through a guide catheter [not shown] and then the patient's body lumen 110 until its distal end lies distal of the arterial plaque 114. Perfusion catheter 130 with sheath 100 attached to its distal end 134 is next inserted into the guide catheter and advanced therethrough over guidewire 200 until the sheath is positioned adjacent to arterial plaque 114 in the patient's body lumen.

Radiopaque marker 136 on distal end 134 of perfusion catheter 130 aids the operating physician in accurately placing the catheter and sheath 100 within body lumen 110 by tracking the progress of the radiopaque marker on an x-ray or similar visualization apparatus.

Once perfusion catheter 130 has been properly positioned with sheath 100 adjacent to arterial plaque 114, guidewire 200 may optionally be withdrawn. Conventional balloon catheter 210 next is inserted within inner lumen 132 of perfusion catheter 130 and advanced over guidewire 200 until balloon 212 on the distal end of the balloon catheter is positioned within sheath 100 with the distal end of the balloon extending past the distal end of the sheath. It is understood that the type of balloon catheter that is employed is dictated by whether guidewire 200 remains within perfusion catheter 130 throughout the procedure or is withdrawn following placement of perfusion catheter 130 and sheath 100. Balloon catheter 210 will typically also have a radiopaque marker 214 to aid the physician in accurately placing balloon 212. Optionally, balloon catheter 210 may also be a perfusion catheter with perfusion holes 218 provided distally and proximally of the balloon 212, which allow uninterrupted blood flow to the brain throughout the entire procedure.

Figure 2B:
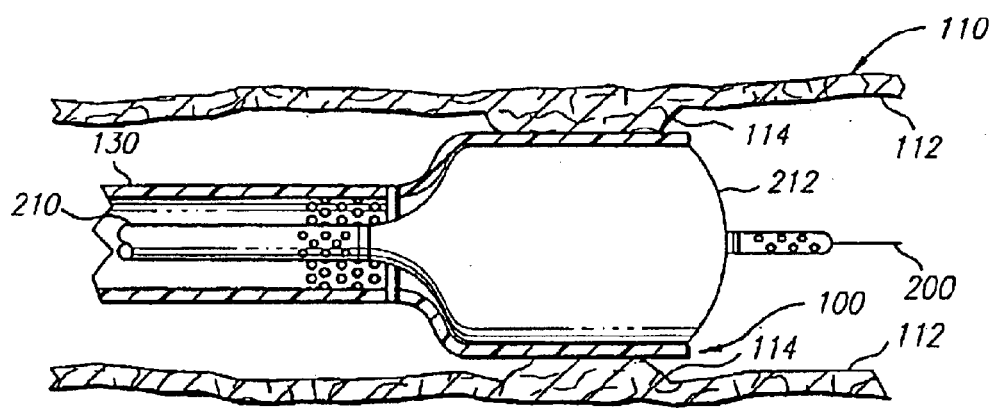
FIG. 2b depicts a side view, partially in cross-section, of the device shown in FIG. 2a with the sheath expanded by the catheter balloon and the plaque shown in FIG. 1 partially compressed against the vascular wall.

Referring now to FIG. 2b, once properly positioned within sheath 100, balloon 212 is inflated to a predetermined pressure. Sheath 100 is expanded by balloon 212 as the balloon is inflated, and therefore the balloon must be inflated with fluid of sufficient pressure to overcome the plastic yield strength of the sheath and thus plastically, or permanently, expand the sheath. Balloon 212 is inflated to a size sufficient to expand sheath 100 against vascular wall 112 and thus compress arterial plaque 114 and trap the plaque against the vascular wall. In this manner any portions of arterial plaque 114 that may have become loose are prevented by sheath 100 from breaking away from vascular wall 112 and embolizing in the blood stream of the patient.

Figure 2C:
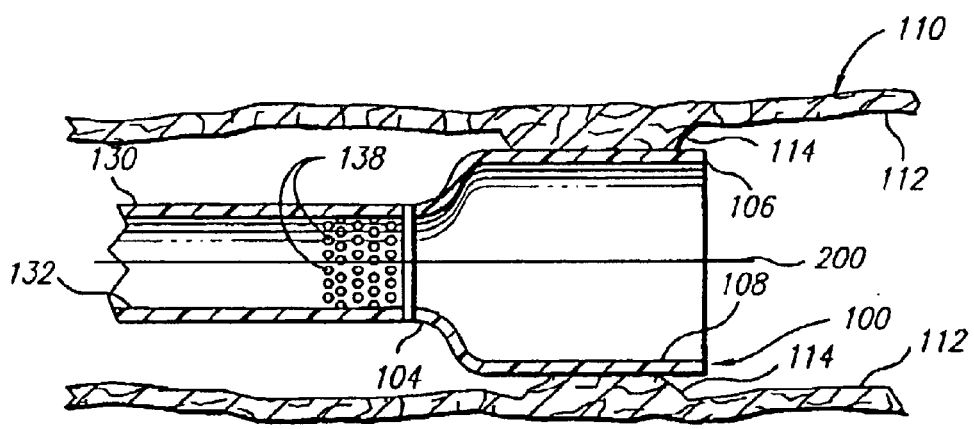
FIG. 2c depicts a side view, partially in cross-section, of the device shown in FIG. 2b with the sheath in an expanded configuration after the balloon catheter has been deflated and withdrawn.

With reference to FIG. 2c, after sheath 100 has been expanded and has trapped arterial plaque 114 against vascular wall 112, balloon 212 is deflated and allowed to regress to its folded configuration, following which balloon catheter 210 is withdrawn from within perfusion catheter 130. At this point perfusion catheter 130 is still located within body lumen 110 to maintain expanded sheath 100 in position to retain arterial plaque 114 against vascular wall 112. At this time perfusion holes 138 allow blood to flow uninterrupted through body lumen 110 by providing a flow channel between proximal end 104 and distal end 106 of sheath 100. Blood thus flows from the outside of perfusion catheter 130 on the proximal side of sheath 100 through perfusion holes 138, into sheath inner lumen 108, out through expanded sheath distal end 106, and on into body lumen 110 on the distal end of the sheath. Providing perfusion holes 138 in perfusion catheter 130 therefore enables use of the device of the present invention over extended periods of time with no adverse effects that may otherwise be induced by throttling off the patient's normal blood flow. This is especially important in applications to the carotid artery, which supplies blood to the brain and which could trigger a stroke or seizure if starved of blood.

Figure 2D:
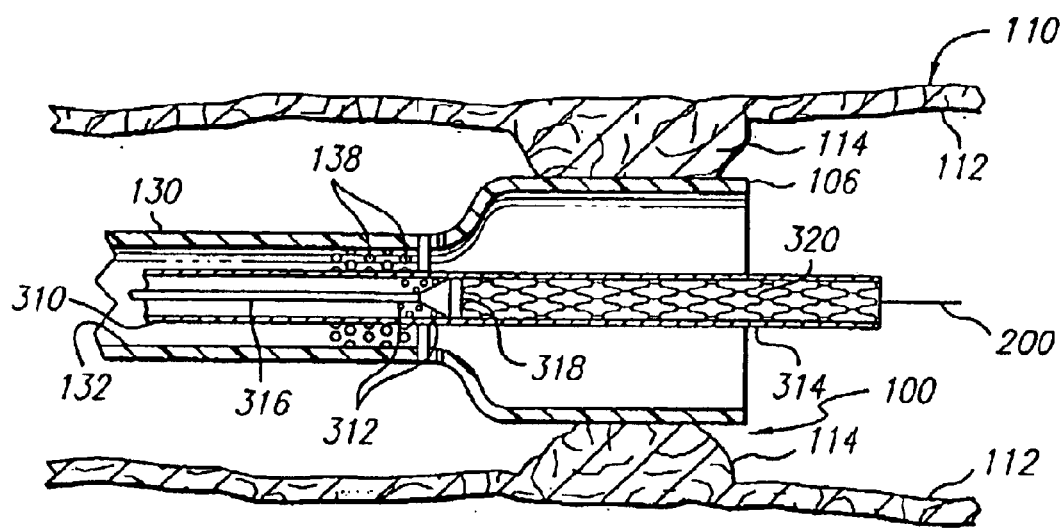
FIG. 2d depicts a side view, partially in cross-section, of the device shown in FIG. 2c with a delivery catheter inserted therethrough and a self-expanding stent disposed within the delivery catheter in a compressed state.

In the next step, as depicted in FIG. 2d, delivery catheter 310 is inserted into interior lumen 132 of perfusion catheter 130. Delivery catheter 310 is of conventional construction and may include perfusion holes 312 to allow blood flow therethrough. Self-expanding stent 320 is disposed within the distal end of delivery catheter 310, which further includes pusher rod 316 disposed within it and adjacent to the stent. Pusher rod 316 is formed with pusher plate 318 mounted at its distal end, and the pusher rod is disposed within delivery catheter 310 such that the pusher plate is adjacent to and in contact with the proximal end of stent 320. If guidewire 200 is utilized to advance delivery catheter 310, then pusher plate 318 and optionally pusher rod 316 must be formed with an appropriately sized lumen [not shown] to permit the guidewire to pass through.

Self-expanding stent 320 can be formed from any number of materials, including metals, metal alloys, and polymeric materials. Preferably, the stents are formed from metal alloys such as stainless steel, tantalum, or the so-called heat-sensitive metal alloys such as nickel titanium (NiTi). When formed from shape-memory alloys such as NiTi, stent 320 will remain passive in its martensitic state when it is kept at a temperature below the transition temperature. In this case, the transition temperature will be below the normal body temperature, or about 98.6° F., and in a preferred embodiment the stent self expands at room temperature. When the NiTi is exposed to normal body temperature upon insertion of delivery catheter 310 into perfusion catheter 130, it will attempt to return to its austenitic state and, if not constrained, will rapidly expand radially outwardly to assume its preformed, expanded state. Alternative shape-memory materials that may be used to form stent 320 include stress-induced martensite (SIM) alloys, which transform into martensite upon the application of stress such as a compressive load, and return to their austenitic, preformed state when the stress is removed.

Stent 320 is thus restrained by delivery catheter 310 from assuming its expanded state, and the delivery catheter wall must be of sufficient thickness to withstand the radially outward expansive forces exerted by the stent upon it. Delivery catheter 310 typically is provided with radiopaque marker 314 to aid the physician in accurately positioning its distal tip relative to sheath 100. The radiopacity of stent 320 also further enhances the visualization of delivery catheter 310 via fluoroscopy. With continued reference to FIG. 2d, upon insertion into interior lumen 132, delivery catheter 310 is advanced through perfusion catheter 130 until it is placed so as to position the distal end of stent 320 outside distal end 106 of sheath 100, and thus distally of plaque 114.

Figure 2E:
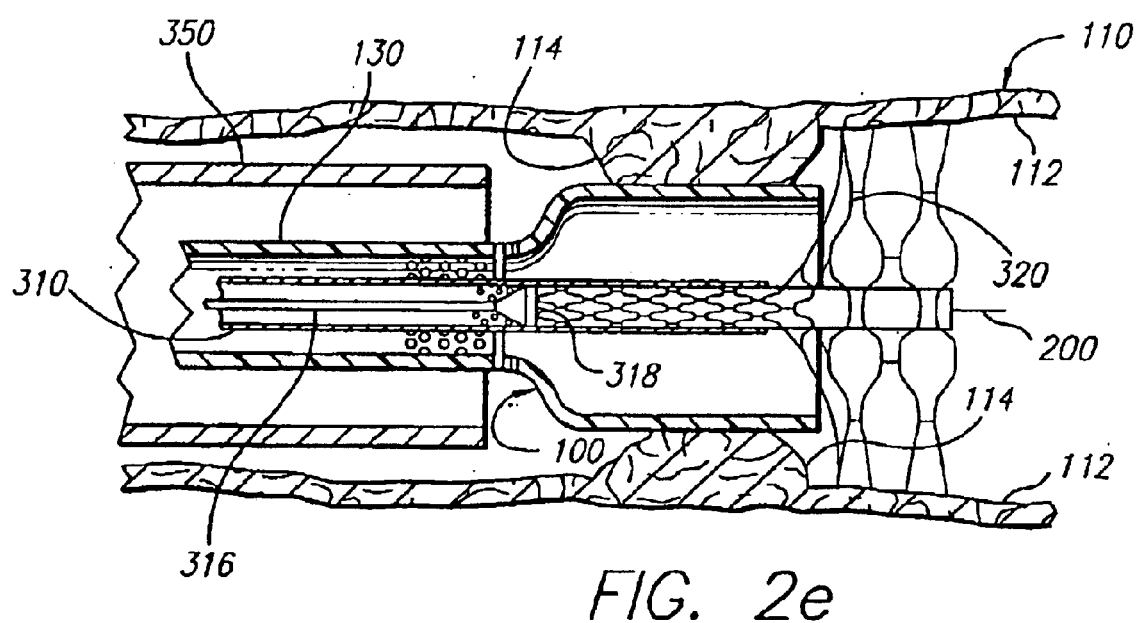
FIG. 2e depicts a side view, partially in cross-section, of the device shown in FIG. 2d with the delivery catheter partially withdrawn and the exposed distal portion of the self-expanding stent in an expanded state contacting the vessel wall at a location distal of the partially compressed plaque.

Referring now to FIG. 2e, the preferred method of deployment entails disposing the distal portion of stent 320 distally of distal end 106 of sheath 100, and thus distally of arterial plaque 114, and then partially retracting delivery catheter 310 proximally to expose the distal portion of the stent. While retracting delivery catheter 310 proximally, pusher rod 316 is immobilized so as to ensure that stent 320 does not travel proximally along with the delivery catheter due to any frictional forces applied by the wall of the delivery catheter as it slides over the stent. Thus, as delivery catheter 310 is retracted proximally, the stent will likely be urged proximally along with it by the friction between the delivery catheter wall and the stent outer surface, but the progress of the stent will be halted by pusher plate 318, which will ensure that the stent remains located at the position initially selected by the physician for deployment.

With continued reference to FIG. 2e, as delivery catheter 310 is retracted, the distal portion of self-expanding stent 320 becomes exposed and, because the restraint applied by the delivery catheter is thereby removed, the radially outward expansive forces exhibited by the stent urge the distal portion of the stent to assume its expanded state, with the distal end of the stent thus expanding to contact the vessel wall 112 at a location distal of the arterial plaque 114. At this point stent 320, although only partially deployed, is in position to intercept any plaque that may come loose and break off from vascular wall 112.

To be able to intercept and retain plaque that may break off, the stent must be designed such that, when in its expanded state, the apertures in the stent wall are no larger than about 200 microns, more preferably no larger than about 50 to 100 microns, and in a preferred embodiment no larger than 25 microns. Thus, the stent may be an expandable tube with slots or other shaped apertures cut therein, or a wire mesh, or a wire coil, or any other practicable self-expanding device. Co-owned U.S. Pat. No. 5,514,154 to Lau et al., U.S. Pat. No. 5,569,295 to Lam, U.S. Pat. No. 5,591,197 to Orth et al., U.S. Pat. No. 5,603,721 to Lau et al., U.S. Pat. No. 5,649,952 to Lam, U.S. Pat. No. 5,728,158 to Lau et al., and U.S. Pat. No. 5,735,893 to Lau et al. describe suitable stents, and these patents are hereby incorporated herein in their entirety by reference thereto. The device of the present invention may also be used in conjunction with other expandable intravascular devices, such as grafts or fine mesh filters that may have a completely or substantially closed outer surface.

Figure 2F:
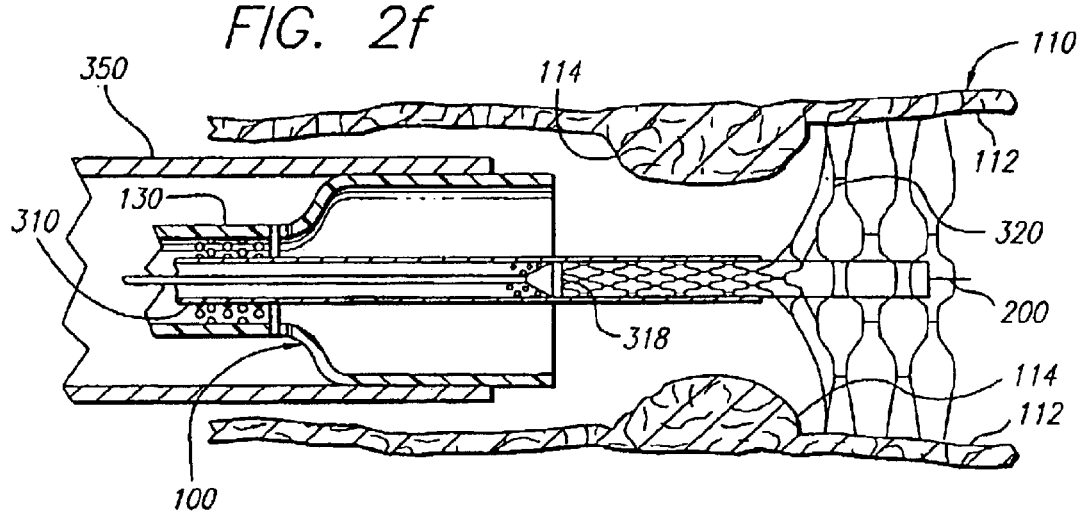
FIG. 2f depicts a side view, partially in cross-section, of the device shown in FIG. 2e with the sheath withdrawn proximally from contact with the plaque to expose the distal tip portion of the delivery catheter.

In the next step, as depicted in FIG. 2f, perfusion catheter 130 is withdrawn proximally to retract sheath 100 from contact with plaque 114 and expose the distal tip of delivery catheter 310 to the plaque. This step presents the potential for portions of plaque 114 breaking off due to the frictional forces between the sliding sheath and the plaque, but because the distal end of stent 320 is deployed against vascular wall 112, any dislodged plaque will be safely intercepted and retained by the stent. The remaining, restricted length of stent 320, which is still disposed within delivery catheter 310, can now be deployed directly against plaque 114.

Figure 2G:
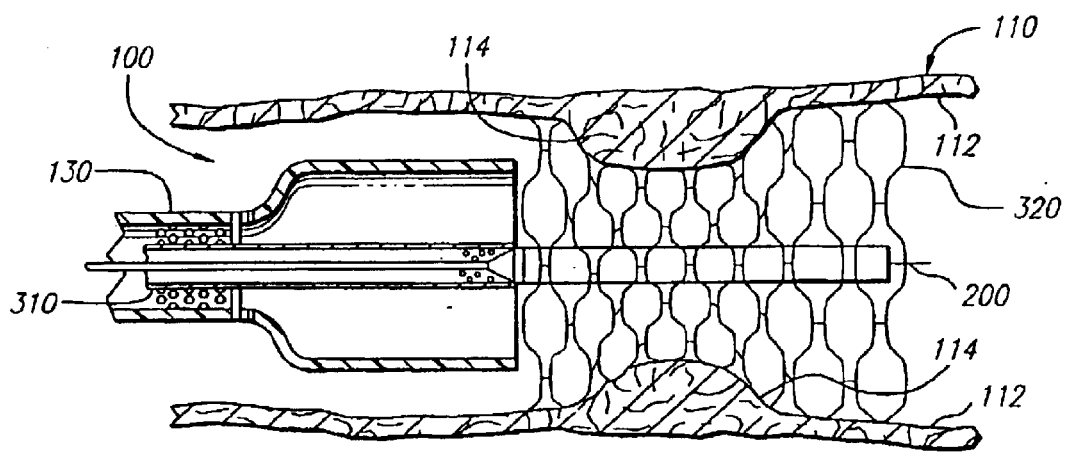
FIG. 2g depicts a side view, partially in cross-section, of the device shown in FIG. 2f with the delivery catheter fully withdrawn and the self-expanding stent in a fully expanded state against the vascular wall to compress and trap the plaque therebetween.

Therefore, as shown in FIG. 2g, in the next step delivery catheter 310 is retracted to expose the entire length of stent 320 and thereby allow the rest of the stent to fully expand against vascular wall 112 and thus further compress and trap arterial plaque 114 therebetween. At this time plaque 114 is safely stabilized against vascular wall 112, the cross-section of the body lumen 110 has been largely restored to about its nominal size, and the procedure is almost completed. In the following steps [not shown in the Figures], guidewire 200, delivery catheter 310, and perfusion catheter 130 are withdrawn from the body lumen, either sequentially or as one unit, and the entry wound into the patient's body is closed. Optionally, prior to withdrawing perfusion catheter 130, the physician may choose to insert a balloon catheter into the perfusion catheter and further expand stent 320 with the balloon to ensure that plaque 114 is sufficiently compressed and/or lumen 110 has been sufficiently expanded.

Referring once again to FIG. 2e, in an alternative embodiment the assembly of the present invention may additionally comprise outer sheath 350, which overlies perfusion catheter 130 and is sized so that when in its expanded state, sheath 100 may be retracted into outer sheath. The principal purpose of outer sheath 350 is to scrape off any plaque that may be adhering to the outer surface of sheath 100, and thus the outer sheath is preferably sized so that, as shown in FIG. 2f, expanded sheath 100 contacts the outer sheath as the expanded sheath is drawn into the outer sheath and thereby dislodges any plaque adhering to the expanded sheath. It would therefore be advantageous if outer sheath is formed of a relatively flexible, compliant material such as PTFE that will expand to accommodate expanded outer sheath 100 as it is drawn into the outer sheath, and thus allow the physician to expand sheath 100 to any desired size during the procedure with no limitations imposed on the maximum expandable size of sheath 100 by outer sheath 350. To further aid the process, proximal end 104 of sheath 100 may be formed with an angled configuration that will more easily slide into outer sheath 350.

Figure 3:
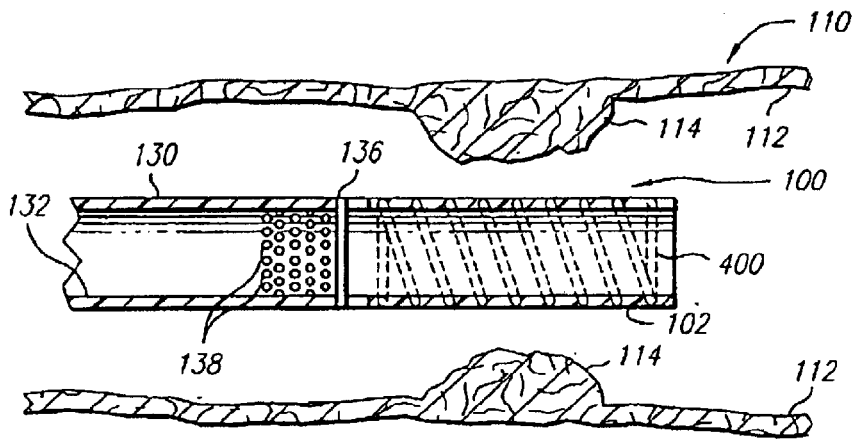
FIG. 3 depicts a side view, partially in cross-section, of the device shown in FIG. 1 a with a coil embedded within the sheath.
Figure 4A:
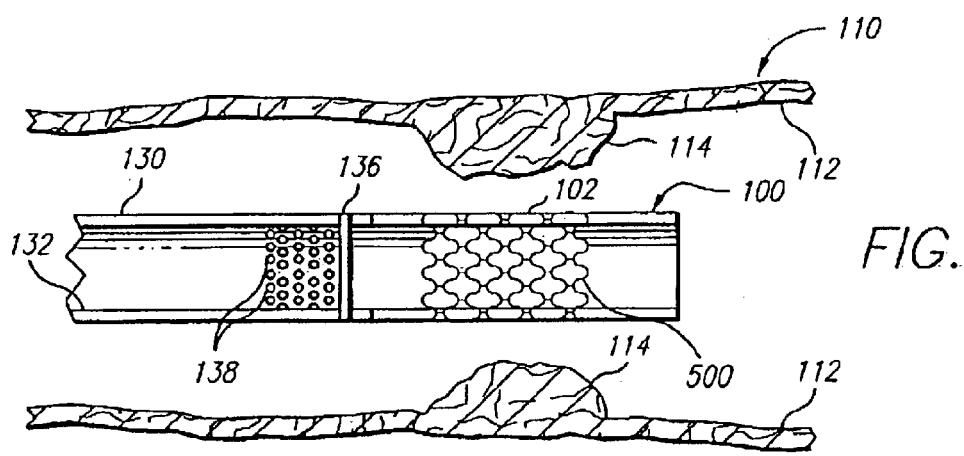
FIG. 4a depicts a side view of the expandable sheath device shown in FIG. 1a with a stent embedded in the sheath.
Figure 4B:
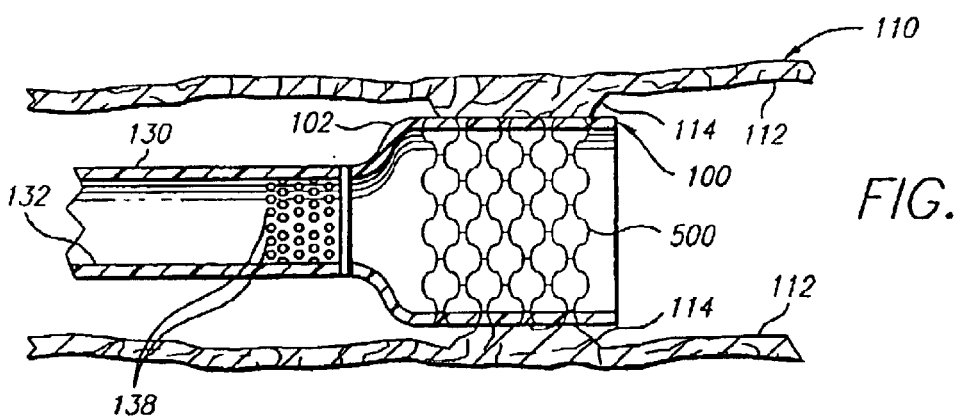
FIG. 4b depicts a side view of the device shown in FIG. 4a with the sheath and the stent embedded therein expanded against the plaque on the vascular wall.

In an alternative embodiment of the device of the present invention, as depicted in FIG. 3, sheath 100 comprises an expandable support element such as helical coil 400 embedded within tubular wall 102. The purpose of coil 400 is to impart additional structural strength and crush resistance to sheath 100, and thus enable the sheath to better support body lumen 110 while a stent or graft is being deployed. An alternative embodiment of an expandable support element is depicted in FIG. 4a, wherein stent 500 is embedded in tubular wall 102. FIG. 4b depicts sheath 100 with stent 500 in an expanded configuration. Such reinforced sheaths may be used to expand body lumen 110 to 100 percent or more of its nominal, unconstricted size.

With continued reference to FIGS. 3 and 4, in an alternative embodiment of the device of the present invention, the expandable support element such as illustrated by coil 400 and stent 500 may comprise materials exhibiting shape memory properties, such as spring steel, Nitinol, superelastic or shape memory nickel-titanium alloys, and resilient engineering plastics such as polysulfones, PEEK, polysulfides, LCPs, etc. In such an embodiment, the expandable support element would be formed to exhibit a radially outward expansive force that is weaker than the force required for plastic deformation of sheath 100 and, preferably, the resistance to elastic deformation of the sheath would be between one and five percent greater than the expansive force exhibited by the support element. The sheath would thus remain in its unexpanded configuration until expanded by a balloon or similar expansion device, as detailed elsewhere in the specification, but would require a lessened degree of expansive force (e.g., a lower balloon inflation pressure) to be deployed into its expanded configuration due to the aiding outward force exhibited by the expandable support element. These embodiments could also be used in conjunction with outer sheath 350, as discussed previously in conjunction with FIGS. 2e & 2f.

In view of the foregoing, it is apparent that the device and method of the present invention enhance substantially the safety of angioplasty procedures by significantly reducing the risk associated with friable plaque deposits breaking away from the vascular wall and migrating into the patient's blood stream to form emboli and potentially cause injury. Further modifications and improvements may additionally be made to the device and method disclosed herein without departing from the scope of the invention. Accordingly, it is not intended that the invention be limited, except as by the appended claims.

What is claimed:

1. A method for entrapping plaque particles against a vascular wall at a predetermined intravascular site, comprising the steps of:

providing a radially outwardly deformable, tubular sheath having a proximal end and a distal end;

providing an intravascular deployment catheter having a proximal end, a distal end, and a lumen extending therebetween;

attaching the sheath proximal end to the deployment catheter distal end;

providing a radially outwardly deformable stent;

disposing the stent within the sheath;

introducing the deployment catheter into the vasculature;

advancing the deployment catheter through the vasculature to position the sheath at the intravascular site; and expanding the sheath against the vascular wall at the intravascular site to trap the plaque therebetween; wherein the step of expanding the sheath comprises expanding the stent along with the sheath, the sheath contacting the vascular wall and the stent contacting the sheath.

2. The method of claim 1, wherein the sheath is formed as a unitary part of a distal tip of the deployment catheter.

3. The method of claim 1, wherein the step of providing an intravascular deployment catheter comprises providing an intravascular deployment catheter having a plurality of perforations formed near the distal end of the deployment catheter to allow fluid communication between the outside of the deployment catheter and the deployment catheter lumen.

4. The method of claim 1, wherein the sheath is comprised of a material selected from the group of materials consisting of polymers, cross-linked materials, and composites.

5. The device of claim 4, wherein the sheath material has a yield strength of between 50 psi and 300 psi.

6. The method of claim 5, wherein the sheath material has a break point tensile strength of over 2000 psi.

7. The method of claim 1, wherein the stent is formed from a shape memory alloy having a compressed state for placing within the unexpanded sheath and an expanded state for anchoring the sheath against the vascular wall, and exhibiting a radially outward expansive force when in the compressed state.

8. The method of claim 7, wherein the resistance to elastic deformation of the sheath is greater than the expansive force exhibited by the stent.

9. The method of claim 8, wherein the resistance to elastic deformation of the sheath is between 1 percent to 5 percent greater than the expansive force exhibited by the stent.

10. The method of claim 1, wherein the stent is formed from a radiopaque material.

11. The method of claim 1, wherein the stent is embedded within the sheath.

12. The method of claim 11, wherein the stent is a wire stent.

13. The method of claim 11, wherein the stent is a wire coiled stent.

14. The method of claim 1, wherein the distal end of the sheath is expanded to a size sufficient to allow a delivery catheter to at least partially deploy and expand an implantable medical device distally from the sheath.

15. The method of claim 1, wherein the sheath is expanded by a balloon catheter.

16. A method for entrapping plaque particles against a vascular wall at a predetermined intravascular site, comprising the steps of:

providing a radially outwardly deformable, tubular sheath having a proximal end and a distal end;

providing an intravascular deployment catheter having a proximal end, a distal end, and a lumen extending therebetween;

attaching the sheath proximal end to the deployment catheter distal end;

introducing the deployment catheter into the vasculature;

advancing the deployment catheter through the vasculature to position the sheath at the intravascular site;

expanding the sheath against the vascular wall at the intravascular site to trap the plaque therebetween;

providing a delivery catheter having a proximal end and a distal end and a lumen extending therebetween;

providing a self-expanding intravascular device having a proximal end and a distal end and further having a compressed state and an expanded state;

placing the intravascular device in its compressed state within the delivery catheter distal end;

introducing the delivery catheter into the lumen of the deployment catheter;

advancing the delivery catheter through the lumen of the deployment catheter to position the distal end of the delivery catheter adjacent the distal end of the sheath;

partially retracting the delivery catheter to allow the distal end of the intravascular device to expand against the vessel wall at a location distal of the plaque at the intravascular site;

withdrawing the sheath proximally from the intravascular site to expose the distal end of the delivery catheter;

retracting the delivery catheter to allow the entire intravascular device to expand against the vessel wall at the intravascular site and trap the plaque therebetween;

withdrawing the delivery catheter from within the intravascular catheter; and withdrawing the intravascular catheter and the sheath from within the vasculature.

17. The method of claim 16, wherein:

the step of providing a delivery catheter further comprises providing a pusher rod disposed within the delivery catheter lumen to contact the proximal end of the intravascular device; and the steps of advancing the intravascular device out of the delivery catheter comprise withdrawing the delivery catheter proximally along the pusher rod to expose the intravascular device and thereby allow it to assume its expanded state.

18. The method of claim 16, wherein the intravascular device is a stent.

19. The method of claim 18, wherein the stent is formed with a plurality of apertures, each aperture being no larger than 200 microns across when the stern is in the expanded state.

20. The method of claim 16, wherein the intravascular device is a wire mesh.

21. The method of claim 20, wherein the wire mesh is formed with a plurality apertures, each aperture being no larger than 200 microns across when the wire mesh is in the expanded state.

22. The method of claim 16, wherein:

the step of expanding the sheath against the vascular wall comprises partially expanding the sheath; and comprising, after the step of withdrawing the delivery catheter, the further steps of:

providing a balloon catheter;

inserting the balloon catheter into the lumen of the deployment catheter;

advancing the balloon catheter to position the balloon within the intravascular device;

inflating the stent to further expand the intravascular device against the vessel wall and entrap the plaque therebetween; and withdrawing the balloon catheter from the deployment catheter lumen.

23. The method of claim 16, wherein the step of providing a delivery catheter comprises providing a delivery catheter with perforations formed near the distal end of the delivery catheter to allow fluid communication between the outside of the delivery catheter and the delivery catheter lumen.

24. A method for entrapping plaque particles against a vascular wall at a predetermined intravascular site, comprising the steps of:

providing a radially outwardly deformable, tubular sheath having a proximal end and a distal end;

providing an intravascular deployment catheter having a proximal end, a distal end, and a lumen extending therebetween;

attaching the sheath proximal end to the deployment catheter distal end;

providing a radially outwardly deformable, tubular member;

disposing the deformable member within the sheath so that the deformable member is embedded into the wall of the sheath;

introducing the deployment catheter into the vasculature;

advancing the deployment catheter through the vasculature to position the sheath at the intravascular site; and expanding the sheath against the vascular wall at the intravascular site to trap the plaque therebetween;

wherein the step of expanding the sheath comprises expanding the deformable member along with the sheath, the sheath contacting the vascular wall.

25. The method of claim 24, wherein the deformable member is a wire mesh.

26. The method of claim 24, wherein the deformable member is a wire coil.

* * * * *

UNITED STATES PATENT AND TRADEMARK OFFICE
CERTIFICATE OF CORRECTION

PATENT NO. : 6,833,002 B2
DATED : December 21, 2004
INVENTOR(S) : Richard S. Stack et al.

It is certified that error appears in the above-identified patent and that said Letters Patent is hereby corrected as shown below:

Column 3,
Line 25, delete "FIG. 1 a" and insert -- FIG. 1a --.

Column 9,
Line 23, delete "stale" and insert -- state --.

Column 10,
Line 37, delete "stern" and insert -- stent --.

Signed and Sealed this

Twelfth Day of July, 2005

JON W. DUDAS
*Director of the United States Patent and Trademark Office*